United States Patent [19]
Cole et al.

[11] Patent Number: 6,142,008
[45] Date of Patent: Nov. 7, 2000

[54] AIR BUBBLE SENSOR

[75] Inventors: Martin A. Cole, San Diego; Michael W. Lawless; Christopher D. Lynch, both of Poway; Frank S. C. Mo, Santa Clara; Peter A. Soberon, San Diego, all of Calif.

[73] Assignee: Abbott Laboratories, Abbott Park, Ill.

[21] Appl. No.: 09/097,068

[22] Filed: Jun. 12, 1998

[51] Int. Cl.$^7$ .............................. G01N 29/02; A61M 5/36
[52] U.S. Cl. ........................... 73/19.03; 73/1.83; 604/65; 604/67; 604/122; 128/DIG. 13
[58] Field of Search ................................ 73/19.03, 61.75, 73/61.79, 64.53, 1.82, 1.83; 600/437, 459; 604/122, 123, 124, 65, 67; 128/DIG. 12, DIG. 13

[56] References Cited

U.S. PATENT DOCUMENTS

| | | |
|---|---|---|
| 3,699,320 | 10/1972 | Zimmerman . |
| 3,731,679 | 5/1973 | Wilhelmson et al. . |
| 3,768,084 | 10/1973 | Haynes . |
| 3,854,038 | 12/1974 | McKinley . |
| 3,898,637 | 8/1975 | Wolstenholme . |
| 3,921,622 | 11/1975 | Cole ................................. 73/61.75 X |
| 3,935,876 | 2/1976 | Massie et al. . |
| 3,974,681 | 8/1976 | Namery . |
| 3,990,444 | 11/1976 | Vial . |
| 4,014,206 | 3/1977 | Taylor . |
| 4,068,521 | 1/1978 | Cosentino et al. ..................... 73/19.03 |
| 4,114,144 | 9/1978 | Hyman . |
| 4,155,362 | 5/1979 | Jess . |
| 4,210,138 | 7/1980 | Jess et al. . |
| 4,213,454 | 7/1980 | Shim . |
| 4,217,993 | 8/1980 | Jess et al. . |
| 4,256,437 | 3/1981 | Brown . |
| 4,280,495 | 7/1981 | Lampert . |
| 4,319,568 | 3/1982 | Tregoning . |
| 4,366,384 | 12/1982 | Jensen . |
| 4,367,736 | 1/1983 | Gupton . |
| 4,394,862 | 7/1983 | Shim . |
| 4,418,565 | 12/1983 | St. John . |
| 4,444,546 | 4/1984 | Pazemenas . |
| 4,447,191 | 5/1984 | Bilstad et al. . |
| 4,487,601 | 12/1984 | Lindermann . |
| 4,496,346 | 1/1985 | Mosteller . |
| 4,501,531 | 2/1985 | Bilstad et al. . |
| 4,607,520 | 8/1986 | Dam . |
| 4,636,144 | 1/1987 | Abe et al. . |

(List continued on next page.)

FOREIGN PATENT DOCUMENTS

| | | |
|---|---|---|
| 0453211 | 10/1991 | European Pat. Off. . |
| 0643301 | 3/1995 | European Pat. Off. . |
| 3530747 | 3/1987 | Germany . |
| 2312046 | 10/1997 | United Kingdom . |
| 7942 | 7/1990 | WIPO . |
| 16087 | 10/1991 | WIPO . |
| 9531233 | 11/1995 | WIPO . |
| 9856441 | 12/1998 | WIPO . |

*Primary Examiner*—Daniel S. Larkin
*Attorney, Agent, or Firm*—Neal D. Marcus

[57] ABSTRACT

A system and a method for detecting the presence of air bubbles in an intravenous (IV) line supplying a medicinal liquid to a patient. An air bubble sensor includes an ultrasonic transmitter acoustically coupled to an ultrasonic receiver to detect the presence of a gas (e.g., air) in a portion of a tube comprising the IV line. The transmitter and receiver are mounted on pivoting transducers that are disposed on opposite sides of the tube. A spring biases the transducers inwardly toward each other so that the transmitter and receiver contact opposite sides of the tubing. This assembly automatically accommodates different sizes of tubing and tubing of a relatively wide range of stiffness. The tube is connected to a disposable pumping cassette that is engaged in a pump chassis on which the transducers are pivotally mounted. A user actuated plunger on the pump chassis is depressed to cause the transmitter and receiver to move away from the tube when the pumping cassette is removed from or inserted into the interior of the pump chassis. A controller precisely monitors the flow of medicinal liquid through the tubing to detect the size of gas bubbles and total volume of gas infused. The controller automatically compensates for minor contamination of the exterior surface of the tube, e.g., if the surface is wet with a liquid.

35 Claims, 13 Drawing Sheets

U.S. PATENT DOCUMENTS

| | | |
|---|---|---|
| 4,648,869 | 3/1987 | Bobo, Jr. . |
| 4,658,244 | 4/1987 | Meijer . |
| 4,668,945 | 5/1987 | Aldrovandi et al. ................ 600/459 X |
| 4,731,057 | 3/1988 | Tanaka et al. . |
| 4,821,558 | 4/1989 | Pastrone et al. .................. 73/61.79 X |
| 4,829,448 | 5/1989 | Balding et al. . |
| 4,874,359 | 10/1989 | White et al. . |
| 4,884,065 | 11/1989 | Crouse et al. . |
| 4,919,596 | 4/1990 | Slate et al. . |
| 4,981,467 | 1/1991 | Bobo, Jr. et al. . |
| 5,000,663 | 3/1991 | Gorton . |
| 5,026,348 | 6/1991 | Venegas . |
| 5,043,706 | 8/1991 | Oliver . |
| 5,053,747 | 10/1991 | Slate et al. . |
| 5,064,412 | 11/1991 | Henke et al. . |
| 5,102,392 | 4/1992 | Sakai . |
| 5,123,275 | 6/1992 | Daoud .................................... 73/19.03 |
| 5,176,631 | 1/1993 | Koenig . |
| 5,219,327 | 6/1993 | Okada . |
| 5,343,734 | 9/1994 | Maeda et al. . |
| 5,394,732 | 3/1995 | Johnson et al. .................... 73/19.03 X |
| 5,429,485 | 7/1995 | Dodge . |
| 5,537,853 | 7/1996 | Finburgh et al. ...................... 73/19.03 |
| 5,755,691 | 5/1998 | Hilborne . |

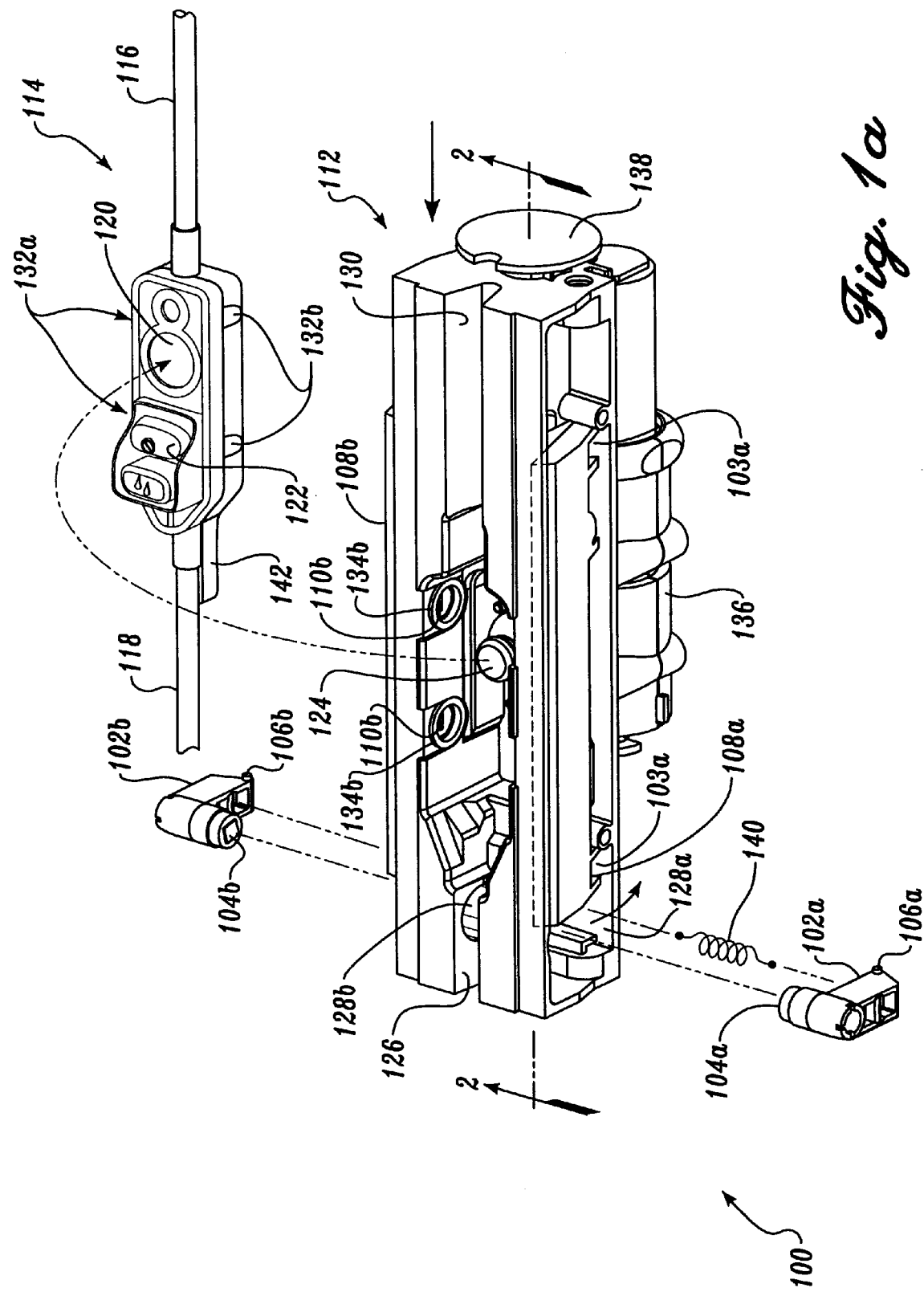

SamplingPercentage = SamplesPerStroke * SampleVolume / StrokeVolume * 100

SamplesPerStroke = StrokeDuration / SamplingInterval

StrokeDuration = (StrokeDegrees / 360) * RotationTime

SamplingInterval = 1.29 / R

= 1.29 / (60 / RotationTime)

SamplesPerStroke = (StrokeDegrees / 360) * RotationTime
 _____
    1.29 / (60 / RotationTime)
   = (StrokeDegrees / 360) * RotationTime * (60 / RotationTime) / 1.29
   = (163 / 360) * 60 / 1.29

SamplesPerStroke = 21.06

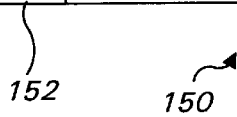

Fig. 8

| TYPE | ID (in) | SAMPLE VOLUME (μl) | SAMPLING PERCENTAGES ||||
|---|---|---|---|---|---|---|
| | | | 1.29/R (126 - 145 ml/hr) | 200 (ml/hr) | 400 (ml/hr) | 1000 (ml/hr) |
| MACROBORE | 0.100 | 5.06 | 142.3 | 103.5 | 51.7 | 20.7 |
| MICROBORE | 0.052 | 1.37 | 41.5 | 30.2 | 15.1 | 6.0 |
| POLY LINED | 0.042 | 0.89 | 25.1 | 18.2 | 9.1 | 3.6 |
| MINIBORE | 0.032 | 0.52 | 14.6 | 10.6 | 5.3 | 2.1 |

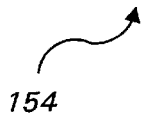

Fig. 9

| VARIABLE | DEFINITION |
|---|---|
| DELTA (201) | VOLUME OF LIQUID OR AIR DELIVERED SINCE PREVIOUS AIR COMPUTATION |
| VOLUME (203) | DELIVERED VOLUME. RISES DURING DELIVERY STROKE ONLY (NOT DURING AIR PURGE OR INTAKE STROKE) |
| PREVIOUS_VOLUME (205) | DELIVERED VOLUME WHEN ALGORITHM WAS LAST INVOKED |
| AIR_BUBBLE (207) | SIZE OF CURRENT AIR BUBBLE IN PROGRESS. RESETS TO 0 IF ENOUGH LIQUID SENSED TO BE CONSIDERED END OF AIR BUBBLE. |
| AIR_VOLUME_THRESHOLD (211) | USER SELECTED AIR BUBBLE SIZE TO TRIGGER ALARM |
| AIR_SIGNAL_THRESHOLD (213) | SIGNAL LEVEL BELOW WHICH AIR IS JUDGED TO BE PRESENT |
| DEFAULT_AIR_SIGNAL_THRESHOLD (217) | 60% OF FACTORY_CALIBRATED_NORMAL_LIQUID_SIGNAL |
| FACTORY_CALIBRATED_NORMAL_LIQUID_SIGNAL (219) | SIGNAL LEVEL WHICH REPRESENTS THE LIQUID INSIDE THE TUBE, AIR OUTSIDE |
| CHECK_CASSETTE_ADC_VALUE (221) | SIGNAL VALUE ABOVE WHICH THE CHECK_CASSETTE_FLAG WILL BE SET |

AIR BUBBLE SENSOR

FIELD OF THE INVENTION

The present invention relates generally to sensing an air bubble in a liquid flowing in an intravenous line, and more particularly, to an air bubble sensor that is automatically positioned on an intravenous line, for determining the size and density of air bubbles in the liquid flowing through the line.

BACKGROUND OF THE INVENTION

In the field of medicine, an intravenous (IV) line is often used to convey a flow of a medicinal liquid into a patient's body. A reservoir containing the medicinal liquid is coupled to a proximal end of the IV line and the distal end is coupled to a large vein of the patient. Also, an IV pump is typically employed with the IV line to precisely control the amount of medicinal liquid delivered to the patient over time. Both peristaltic and disposable cassette pumps are commonly used for this purpose. Most IV pumps employ a sensor to detect the presence of air bubbles in the medicinal liquid carried by the IV line to the patient. If the medicinal fluid carries a large air bubble or a series of smaller air bubbles that can combine within the blood stream, the patient may be exposed to a health risk, since the bubble(s) may produce a life threatening air embolism within the patient's cardiovascular system.

A common problem associated with IV pumps is determining the amount of air in the liquid flowing through the IV line. Also, air bubbles that mix with the medicinal liquid reduce the amount of the medicinal liquid delivered to the patient. Typically, the volume of liquid actually delivered to the patient is determined by measuring the liquid-to-air ratio over a predetermined number of IV pumping cycles. Mechanical failures of a pumping cassette in an IV pump and/or a relatively slow liquid flow are frequently the source of air in the IV line.

In the prior art, an air bubble sensor is usually disposed at a fixed position in a housing of an IV pump. A typical prior art air bubble sensor includes two piezoelectric crystals that are mounted on each side of a slot adapted for gripping a portion of an IV line (tubing). The tubing is forced into the slot so that it is held in close association with the inner surfaces of each side of the slot. In some prior art designs, the IV pump includes an access door that is opened to enable the user to force the tubing into the slot. However, the access door increases the number of parts and the cost of manufacturing an IV pump. Also, forcing the tubing into the slot and operating (opening/closing) the access door increases the likelihood of damage to the tubing. Moreover, since the slot is specifically sized for a particular diameter and type of tubing, medical personnel must stock several different pump models (each with housings having a different slot size) to accommodate the various types and sizes of tubing that may be used. Also, tubing sets with the same external diameter, but having different internal diameters exhibit different stiffness characteristics and may require air bubble sensors specifically designed to accommodate tubing having a specific range of stiffness. Variations in the stiffness due to the use of different compositions of material can also cause problems when forcing the tubing into the slot of conventional air bubble sensors.

In a typical air bubble sensor used on an IV pump, one of two piezoelectric crystals (a transmitter) is excited with an electrical signal at the resonant frequency of the crystal to produce an ultrasonic sound wave, which is directed transversely through the IV line towards the other piezoelectric crystal (a receiver), which is disposed on the opposite side of the IV line. The receiver crystal resonates at approximately the same frequency as the transmitter crystal, and in response to the ultrasonic sound waves that it receives, the receiver produces a corresponding electrical signal that is proportional to the amplitude of the sensed ultrasonic waves. Since it is well known that the transmission of ultrasonic sound waves through a liquid is substantially greater than through a gas, any gaseous (air) bubbles entrained in the liquid flowing through the IV line at the point between the transmitter crystal and the receiver crystal will attenuate the ultrasonic sound waves in proportion to the size and density of the bubbles. Thus, a strong electrical signal produced by the receiver crystal indicates that only a liquid is flowing through the portion of the tubing disposed between the transmitter and receiver crystals, while a weak or missing signal indicates the presence of a gas.

Each change in the magnitude of the ultrasonic sound waves received by the receiver crystal causes a corresponding change in the electrical signal that it produces. Usually, a controller is employed to monitor the electrical signal produced by the receiver crystal, for detecting the presence of air bubbles in the medicinal liquid. The controller generates an alarm and/or stops the IV pump when it detects an air bubble larger than a predetermined maximum or too many relatively smaller gas bubbles passing between the transmitter and receiver crystals over a predetermined time period. However, prior art controllers are susceptible to error when the outer surface of the portion of the tubing disposed between the transmitter and receiver crystals is contaminated with a liquid, i.e., if the tubing is wet. The water on the outer surface of the tubing conveys the ultrasound signal between the transmitter and the receiver crystals, causing a false indication of liquid in the line when air bubbles are actually present.

Based on the foregoing discussion, it will be apparent that a more convenient technique for engaging an IV line with an air bubble sensor would be desirable. Ideally, it should not be necessary for a user to force the IV tubing between the transmitter and receiver crystals of the sensor. Different pumps should not be required to accommodate different size IV tubing in the air bubble sensor slot. There should be no need to open an access door in order to facilitate engaging the IV line with the air bubble sensor. Furthermore, the accuracy of an air bubble sensor should not be affected by the presence of liquid on the exterior surface of the line between the transmitter and receiver crystals, since ambulatory IV pumps that may be worn by a patient while bathing or showering will be exposed to moisture that might cause such errors and fail to indicate a potentially hazardous amount of air in the IV line. Since the prior art air bubble sensors have not properly addressed these problems, it will be apparent that there is a need for a novel air bubble sensor that does.

SUMMARY OF THE INVENTION

In accord with the present invention, a system is defined for automatically detecting a gas bubble in a liquid flowing through a tube of an intravenous line. The system includes a chassis that defines a slot, and this slot is substantially wider than a diameter of the tube. An ultrasonic transmitter produces an ultrasonic signal that is directed through a portion of the tube disposed within the slot. The ultrasonic transmitter is disposed adjacent a side of the portion of the tube. On an opposite side of this portion of the tube, directly opposite the ultrasonic transmitter is disposed an ultrasonic receiver for receiving the ultrasonic signal and producing a corresponding electrical signal. A pair of members are pivotally connected to the chassis and are disposed adjacent opposite sides of the slot. One member has an end facing toward the slot, and the ultrasonic transmitter is disposed on that end. Similarly, the other member has an end facing toward the slot, and the ultrasonic receiver is disposed on that end. The pair of members pivot to position the ultrasonic transmitter and the ultrasonic receiver against the sides of the portion of the tube, so that tubes of different type (e.g., different size/stiffness) are accommodated. A controller is coupled to the ultrasonic transmitter to excite the ultrasonic transmitter at a resonant frequency, causing it to produce the ultrasonic signal. The controller is also coupled to the ultrasonic receiver to receive the electrical signal that it produces in response to the ultrasonic signal; the controller responds to a magnitude of the electrical signal to determine whether a liquid or a gas is in the portion of the tube disposed between the ultrasonic receiver and the ultrasonic transmitter.

Another aspect of the present invention is directed to a method for detecting a gas bubble in a tube for an IV line. The method employs steps that are generally consistent with the functions of the systems discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1a is an isometric view of an air bubble sensor in accord with the present invention showing it in use on an IV pump chassis that drives a pumping cassette, and showing a disposable pumping cassette coupled to an IV line monitored by the air bubble sensor;

FIG. 8 is a table of equations for describing the number of samples performed by the control system for each stroke of the pumping cassette;

FIG. 9 is a table of characteristic parameters for several different types of IV tubing;

FIG. 10 is a table of definitions for variables used by the control system for the air bubble sensor;

DESCRIPTION OF THE PREFERRED EMBODIMENT

Figure 1B:
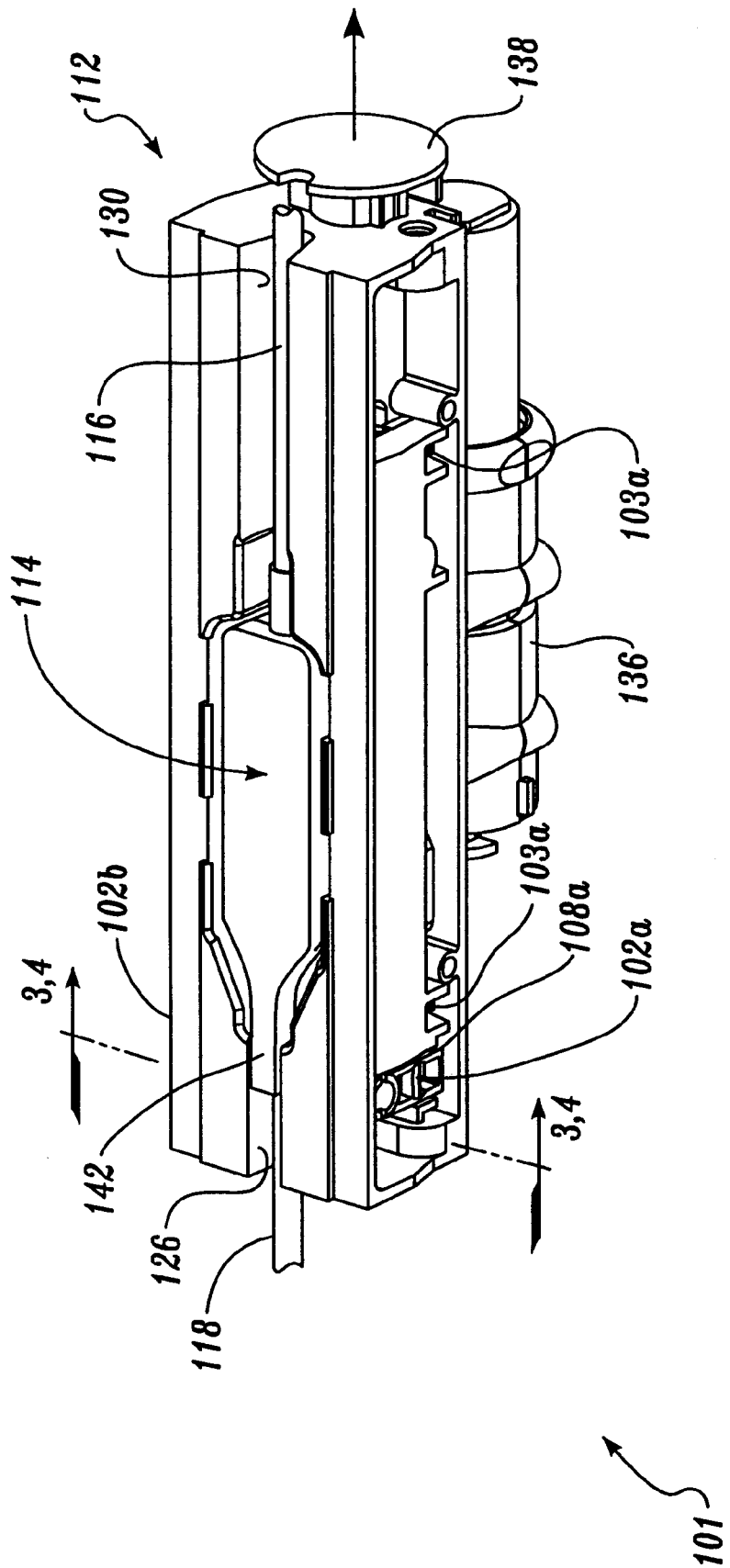
FIG. 1b is an isometric view of the air bubble sensor of FIG. 1a, showing the pumping cassette engaged by the IV pump chassis.

The present invention, preferably, includes an ultrasonic sensor that determines whether air bubble(s) or a liquid is flowing through an IV line coupled to an IV pump. This ultrasonic sensor, which is of a type discussed above in the Background of the Invention, is disclosed in detail in commonly assigned U.S. Pat. No. 4,821,558 (Pastrone et al.), the drawings and disclosure of which are hereby specifically incorporated herein by reference.

While the reader may refer to the above-noted patent, it may be helpful at this point to briefly summarize certain aspects of the air bubble sensor used in a preferred embodiment of the present invention. Generally, the air bubble sensor employs a transmitting crystal, which is excited at its resonant frequency (700 kHz), to produce a corresponding high frequency ultrasonic signal that is directed toward a receiving crystal. The transmitting crystal and receiving crystal are firmly pressed against opposite sides of a portion of tubing (about one mm in length) comprising an IV line. The receiving crystal responds to the ultrasonic signal by vibrating at its corresponding resonant frequency and produces an electrical signal that is amplified and supplied to a controller. If the IV tubing is full of liquid, the magnitude of the electrical signal produced by the receiving crystal is substantially greater than if air is present in the IV tubing. It will be apparent that the signal produced by the receiving crystal can also be relatively low in magnitude or absent if the air bubble sensor has malfunctioned. As described in greater detail below, the present invention automatically compensates for changes in the magnitude or level of the receiving crystal's electrical signal when the outer surface of the portion of the tubing monitored by the air bubble sensor is wetted with a liquid.

FIG. 1a displays an intravenous pump assembly 100 that employs a transmitter 104a and a receiver 104b to detect air bubbles in a portion of a distal tubing 118 comprising a portion of the IV line. Transmitter 104a includes the transmitting crystal discussed above, and receiver 104b includes the receiving crystal. Disposed within the IV line is a pumping cassette 114. Pumping cassette 114, which includes an elastomeric diaphragm 120 and a flow stop 122, is connected between a proximal tubing 116 and distal tubing 118. A tang 142 disposed on the lower portion of the pumping cassette, at its distal end, facilitates positioning and guiding distal tubing 118 into a slot 126 disposed at the distal end of a pump chassis 112 into which the pumping cassette is inserted and engaged.

The interior of pump chassis 112 is adapted to hold pumping cassette 114 and position a reciprocating plunger 124 against the surface of elastomeric diaphragm 120. A prime mover or electric motor 136 is coupled to a linkage (not shown) that reciprocatively drives plunger 124 against elastomeric diaphragm 120 when the motor rotates a cam (not shown) that is coupled to the plunger. A pair of latches 110b are positioned within a pair of ports 134b that are disposed in a side wall of pump chassis 112. Although not shown in this Figure, a pair of latches 110a are positioned within a pair of ports 134a that are disposed in an opposite side wall of pump chassis 112. When pumping cassette 114 is inserted into pump chassis 112, the pairs of latches 110a and 110b are fully extended from within respective ports 134a and 134b, so that the latches grip (latch) notches 132b formed on the side of pumping cassette 114, firmly holding the pumping cassette at a predetermined position within the pump chassis interior. Conversely, when pairs of latches 110a and 110b are retracted into their respective ports 134a and 134b, they disengage from pumping cassette 114, so that it may be removed from the interior of pump chassis 112.

An elongate member 108a extends generally parallel to the longitudinal axis of pump chassis 112, on one side thereof, and latches 110a are disposed on an inwardly facing surface of the member. Member 108a is pivotally connected to pump chassis 112 by a pair of hinges 103a that are disposed at opposed ends of the member's bottom edge. Similarly, an elongate member 108b extends generally parallel to the longitudinal axis of pump chassis 112, at an opposite side of pump chassis 112 from member 108a, and pair of latches 110b are disposed on an inwardly facing surface of member 108b, which is pivotally connected to the pump chassis by a pair of hinges (not shown).

A linkage (not shown) is coupled to members 108a and 108b and to a user actuated plunger 138. User actuated plunger 138 is disposed at a proximal end of pump chassis 112. When the user actuated plunger is depressed in the direction of the arrow, as shown in FIG. 1a, the linkage to which it is coupled causes members 108a and 108b to pivot about hinges 103a and 103b, outwardly and away from the interior of the pump chassis, at both sides. When members 108a and 108b pivot outwardly in this manner, latches 110a and 110b move (retract) through ports 134a and 134b so that the latches are not extended into the interior of pump chassis 112. When pumping cassette 114 is inserted into the interior of pump chassis 112, user actuated plunger 138 moves outwardly of the proximal end of pump chassis 112, and members 108a and 108b pivot about hinges 103a and 103b towards the interior of the pump chassis. This pivoting by members 108a and 108b causes latches 110a and 110b to be moved (extended) through ports 134a and 134b and into engagement with the pumping cassette. Latches 110a and 110b then engage notches 132a and 132b formed on the opposite sides of the pumping cassette, and hold the cassette at a predetermined position, as shown in FIG. 1b. The linkage moves user actuated plunger 138 to the default position, which is shown in FIG. 1b.

Referring again to FIG. 1b, a pair of L-shaped transducers 102a and 102b are disposed on opposite sides of the distal end of pump chassis 112. The longer portions of transducers 102a and 102b are pivotally connected to the sides of pump chassis 112 by hinge pins 106a and 106b, respectively, which extend outwardly of the sides of the transducers and engage orifices (not shown) in the pump chassis. Transmitter 104a is disposed on the shorter portion of transducer 102a, while receiver 104b is disposed on the shorter portion of transducer 102b. Opposed ports 128a and 128b disposed on opposite sides of the pump chassis receive transmitter 104a and receiver 104b, respectively. The transmitter and receiver are then disposed on opposite sides of distal tubing 118 disposed within slot 126, when the pumping cassette is engaged in the pump chassis. A helical spring 140 is connected between transducers 102a and 102b, so that transmitter 104a and receiver 104b are biased against the sides of differently sized distal tubing disposed in slot 126. Additionally, it is contemplated that instead of helical spring 140, another type of biasing element may be employed for this purpose, such as an elastomeric band or a torsion spring. Thus, transmitter 104a and receiver 104b contact opposite sides of a substantial range of different diameter IV lines, unlike prior art air bubble sensors that are limited to functioning with only a very limited range of diameter/stiffness in the IV lines. More importantly, the transmitter and receiver are able to accommodate tubing of differing stiffness, since the internal diameter of the tubing or the stiffness of the material from which the IV line is made does not impact on the ability of the transmitter and receiver of the present invention to accommodate the tubing and make good contact with it. In contrast, it may be difficult to force relatively stiff tubing of an IV line into a fixed width slot of a prior art air bubble sensor.

In FIG. 1b, pumping cassette 114 is disposed in the interior of pump chassis 112 at the predetermined position. Plunger 138 is disposed in the default position, in which it extends outward from the proximal end of pump chassis 112, and members 108a and 108b are pivoted towards the sides of the pump chassis to engage the pumping cassette. Tang 142 is disposed within slot 126 and distal tubing 118 is positioned between ports 128a and 128b in the slot. Helical spring 140 biases transmitter 104a and receiver 104b towards opposite sides of distal tubing 118, which is centered therein, extending transversely between the transmitter and the receiver. Although not shown in this view, diaphragm 120 is in contact with plunger 124 so that reciprocation of the plunger forces medicinal liquid to flow through the pumping cassette when motor 136 is energized.

Figure 2:
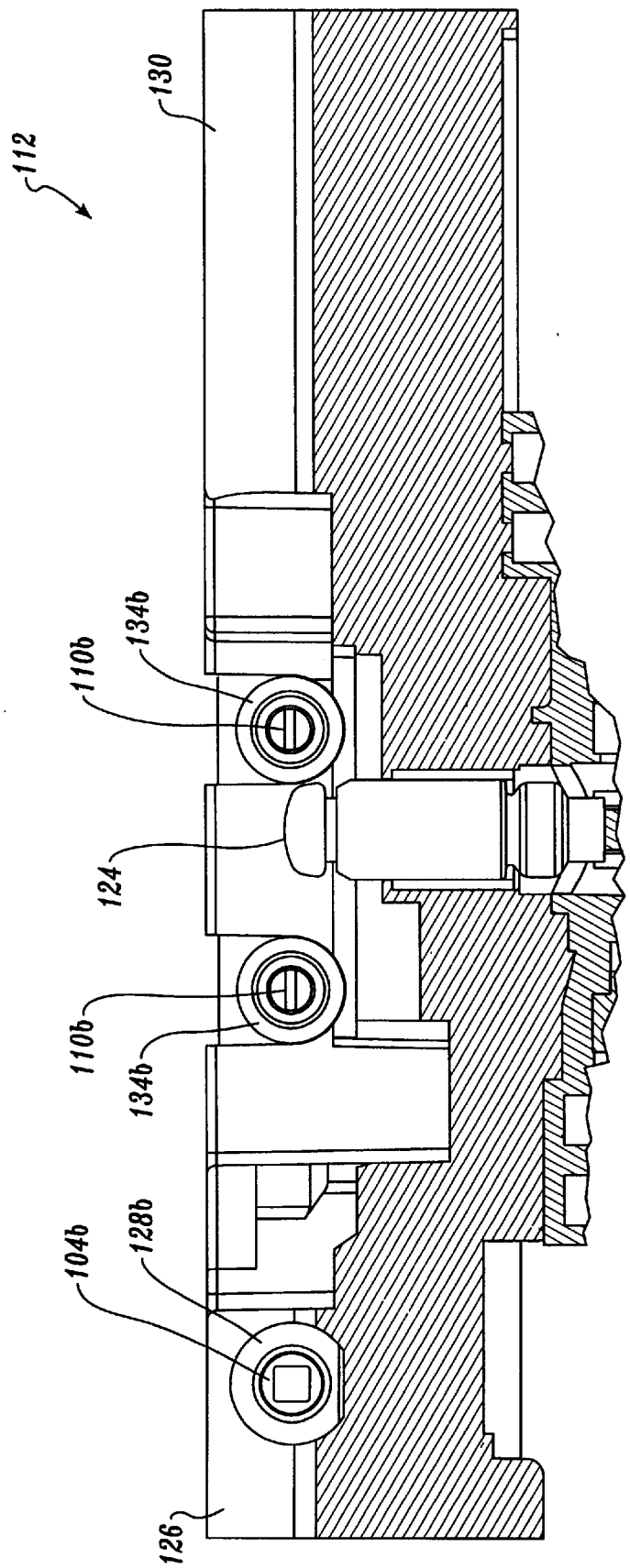
FIG. 2 is a cross-sectional side view taken along a section line 2—2 in FIG. 1a, along the longitudinal axis of the pump chassis.

FIG. 2 is a cross-sectional view taken along section line 2—2 of pump chassis 112. A slot 130 is positioned at the proximal end of pump chassis 112 and slot 126 is positioned at the distal end of the pump chassis. Plunger 124 is positioned transversely to the interior of pump chassis 112 and the pair latches 110b are disposed inside the pair of ports 134b. Also, receiver 104b is withdrawn from the interior of pump chassis 112 at a position inside port 128b.

Figure 3:
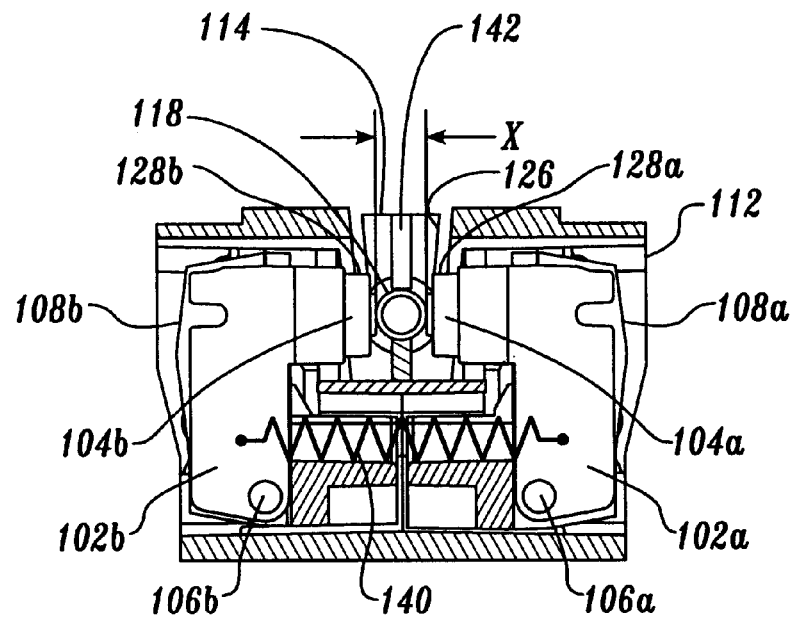
FIG. 3 is a cross-sectional view taken along a section line 3—3 in FIG. 1b, transverse to the distal portion of the pump chassis, showing an IV tubing having a relatively small diameter.

FIG. 3 illustrates how pumping cassette 114 is positioned when engaged in pump chassis 112 and shows how tang 142 keeps distal tubing 118 centered within slot 126. Members 108a and 108b contact opposite sides of pump chassis 112, causing latches 110a and 110b to hold pumping cassette 114 at the predetermined position within the pump chassis interior. Distal tubing 118 is positioned midway between ports 128a and 128b. Helical spring 140 biases transducers 102a and 102b to pivot inwardly on hinge pins 106a and 106b, towards distal tubing 118, so that transmitter 104a and receiver 104b are automatically properly positioned against the opposing sides of the distal tubing. Although a width of distal slot 126 is substantially greater than a diameter (X) of distal tubing 128, the biasing provided by helical spring 140 ensures that transmitter 104a and receiver 104b remain in contact with opposite sides of the distal tubing.

Figure 4:
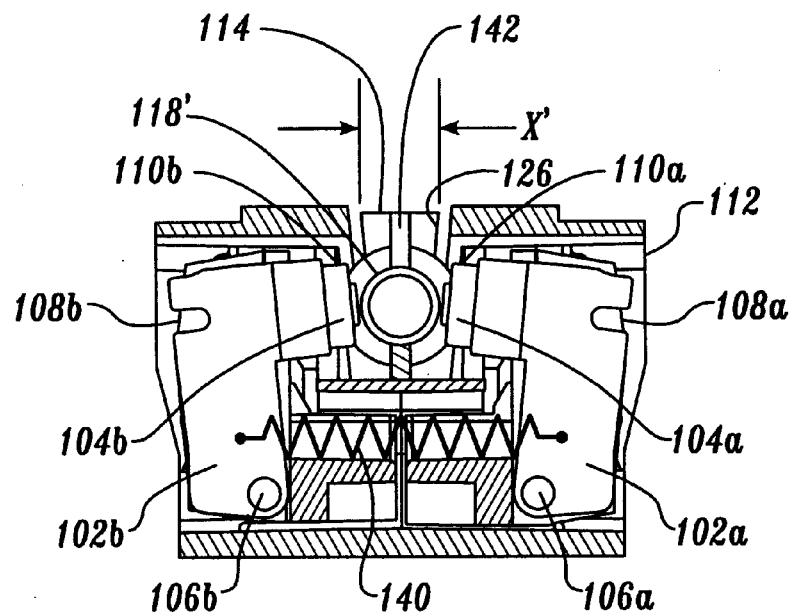
FIG. 4 is a cross-sectional view taken along a section line 4—4 in FIG. 1b, transverse to the distal portion of the pump chassis, showing an IV tubing having a relatively larger diameter than that of FIG. 3.

FIG. 4 is similar to FIG. 3 except that a diameter (X') of a distal tubing 118' is substantially greater than the diameter (X) of distal tubing 118. Also, in FIG. 4, it will be evident that transducers 102a and 102b are pivoted outwardly away from their positions in FIG. 3, to new positions, thereby accommodating the greater diameter of distal tubing 118'.

Although pumping cassette 114 is gripped by latches 110a and 110b, which are disposed on members 108a and 108b, respectively, when pumping cassette 114 is engaged by pump chassis 112, transducers 102a and 102b are free to pivot about hinge pins 106a and 106b and move independently of the members. Helical spring 140 biases transmitter 104a and receiver 104b against opposing sides of distal tubing 118' so that the presence of air bubbles in the tubing center may be detected. It is important to note that transducers 102a and 102b pivoted outwardly away from the distal tubing, when user actuated plunger 138 is depressed to release the pumping cassette from the pump chassis.

Figure 5:
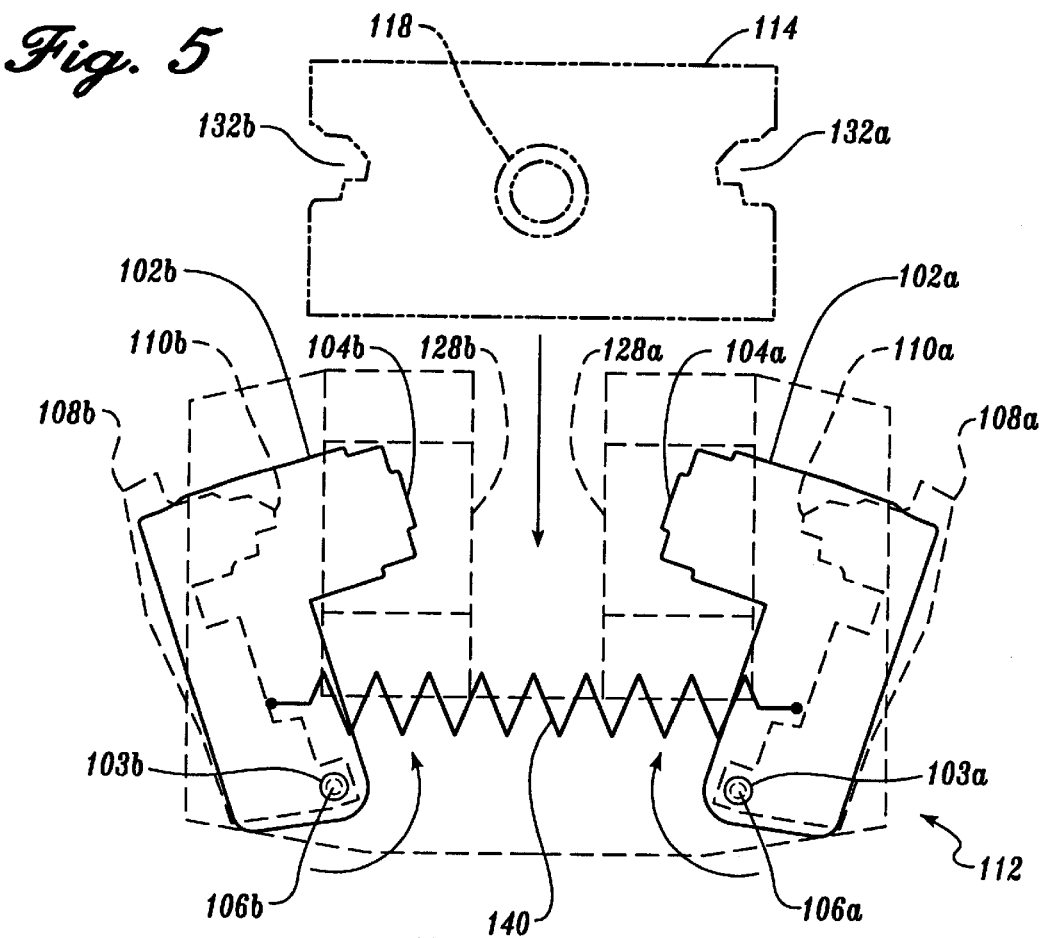
FIG. 5 is a schematic cross-sectional view, transverse to the distal end of the pump chassis, showing the disposable pumping cassette and IV tubing prior to the insertion of the pumping cassette into the interior of the pump chassis.

In FIG. 5, the positions of members 108a and 108b and transducers 102a and 102b, prior to inserting pumping cassette 114 into the interior of pump chassis 112, are schematically illustrated. Although not shown in this view, user actuated plunger 138 is then pushed inwardly toward the proximal end of pump chassis 112, so that the linkage causes the pair of latches 110a and 110b and transducers 102a and 102b to be pivoted away from the interior of the pump chassis and slot 126, respectively. By employing user actuated plunger 138 to retract the pair of latches 110a and 110b and pivot transducers 102a and 102b outwardly, the task of removing the pumping cassette from the pump chassis is much simplified. When inserting the pumping cassette, the action and the resulting force of the pumping cassette against the latches automatically initially opens the transducers outwardly, to facilitate insertion of the tubing into the slot.

Figure 6:
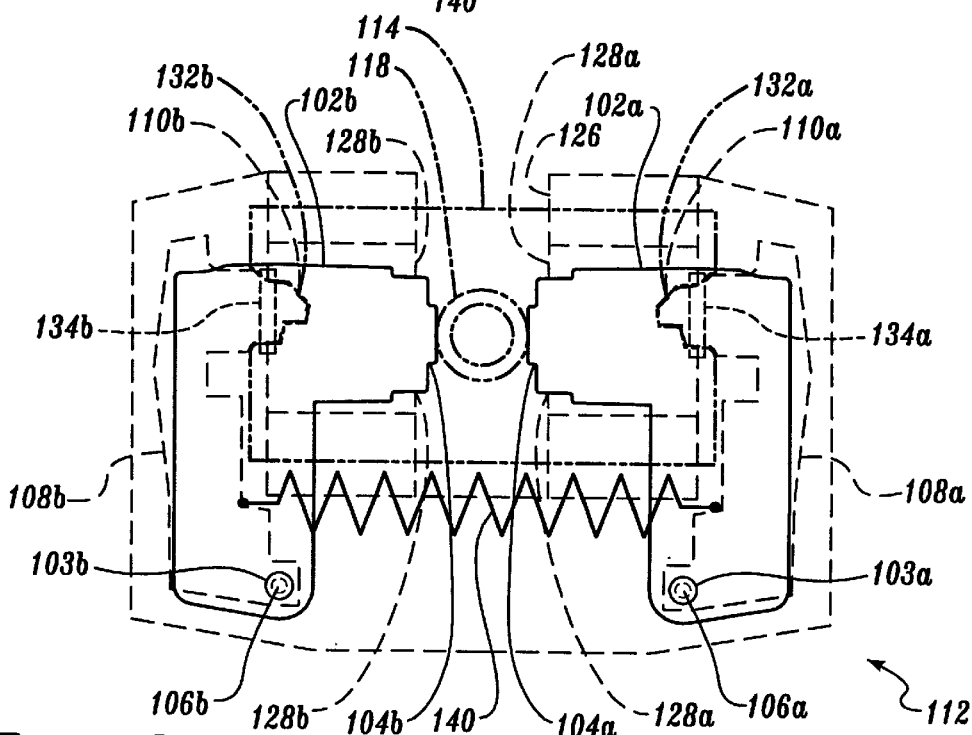
FIG. 6 is a schematic cross-sectional view, transverse to the distal end of the pump chassis, showing the pumping cassette disposed in (and engaged by) the pump chassis.

FIG. 6 is another schematic view, showing members 108a and 108b and transducers 102a and 102b after pumping cassette 114 has been inserted into and engaged in the interior of pump chassis 112. Pumping cassette 114 is gripped at the predetermined location by latches 110a and 110b, which engage notches 132a and 132b, respectively, in the sides of the pumping cassette. The shorter portions of transducers 102a and 102b are disposed in respective ports 128a and 128b and transmitter 104a and receiver 104b are biased by spring 140 against the opposite sides of distal tubing 118.

Control System

Figure 7:
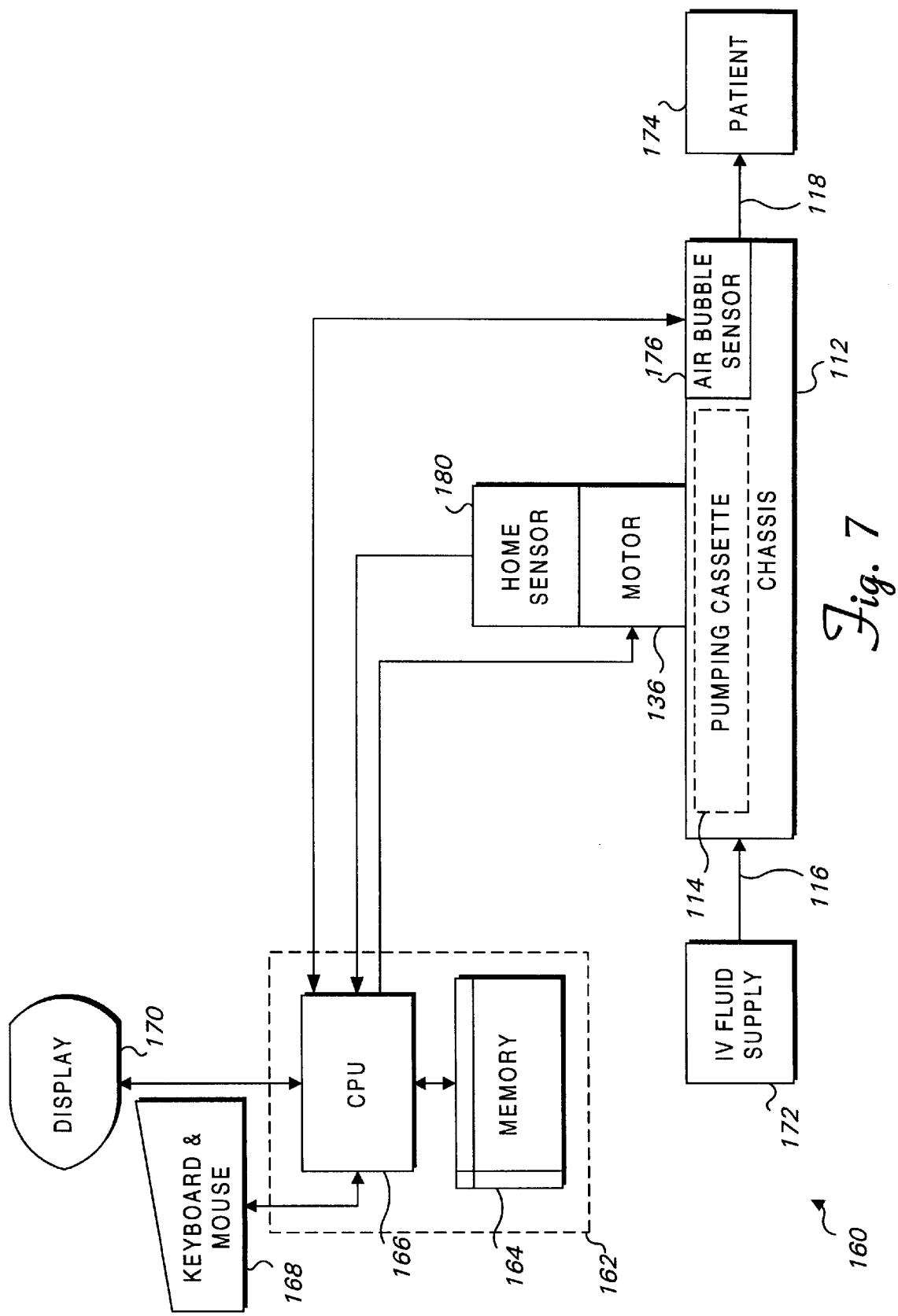
FIG. 7 is a schematic functional block diagram that illustrates a control system for the air bubble sensor.

In FIG. 7, an overview 160 of the medicinal fluid infusion system illustrates the control system for an air bubble sensor 176, which includes transducers 102a and 102b and transmitter 104a and receiver 104b. An intravenous medicinal liquid supply 172 is connected to proximal tubing 116 and supplies a medicinal liquid to pumping cassette 114, which is latched in pump chassis 112. Motor 136 is drivingly coupled to pumping cassette 114 so that the medicinal liquid may be pumped to a patient 174 through distal tubing 118. The position of a drive shaft (not shown) of motor 136 in the pumping cycle of pumping cassette 114 is detected by a home sensor 180 that is coupled to a controller 162, which includes a central processing unit (CPU) 166 and a memory 164. Also, a display 170 and an input device 168, e.g., a keypad or keyboard, are connected to controller 162 to provide an interface for the user. In some IV systems, the IV pump may be coupled to a personal computer, so that the input device can include a mouse or other pointing device.

In one embodiment, home sensor 180 is an optical encoder coupled to the drive shaft of motor 136 for detecting a home position of the drive shaft. Typically, each pump stroke infuses 75 micro liters ($\mu$l) and is divided into 432 pulses (216 pulses for fill and 216 pulses for flow). The large number of pulses enables a high level of precision in delivery of the medicinal liquid and reduces the likelihood of needle clotting in the patient's body. Power consumption of the IV pump is reduced by employing single pole excitation for air bubble sensor 176 and only supplying power to the air bubble sensor when motor 136 is energized.

Generally, when motor 136 is actuating pumping cassette 114, controller 162 controls the sampling by air bubble sensor 176 over a portion (one mm in length) of distal tubing 118. Controller 162 determines whether each sample is either 100% air or 100% liquid by comparing a sampled signal from air bubble sensor 176 to a predetermined threshold that is a fixed percentage of a last reading that was found to indicate the presence of liquid in distal tubing 118. If the sampled signal is valid and below the predetermined threshold, controller 162 determines that the sample indicates the presence of air. Conversely, if a valid sampled signal is above the predetermined threshold, controller 162 determines that the sample indicates the presence of a liquid in the distal tubing. Controller 162 accumulates the volume associated with each sample as delta values used to determine the total liquid volume and the total air volume.

The present invention employs each sample as a representative approximation of the unsampled portion of distal tubing 118 that precedes the current sampling, and the air sampling time intervals approximate the unsampled time intervals. Controller 162 determines the sampling time interval (in seconds) for continuous rotation of motor 136 using the ratio of 1.29/R (R=RPM of the motor's output drive shaft). However, there are high and low limits to the sampling time interval. For example, if pumping cassette 114 is pumping at high rates (e.g., 1000 ml/hr) and the sampling time interval is less than 40 milliseconds, controller 162 sets the sampling time interval to 40 milliseconds. Further, if pumping cassette 114 is pumping at low rates (e.g., less than 126 ml/hr), the sampling time interval is set at 32 milliseconds, which is based on a value for R=60 RPM. Ideally, the sampling time interval begins when valves (not shown) in pumping cassette 114 open and the interval ends when the valves close. The disposition of the valves in pumping cassette 114 is inferred from the position of the drive shaft of motor 136, which is sensed by home sensor 180.

Controller 162 turns off the power to air bubble sensor 176 when motor 136 is not actuating pumping cassette 114. When controller 162 turns the power on to air bubble sensor 176, approximately one millisecond of warm up time is needed before the sensor may be used. Controller 162 checks the output signal from air bubble sensor 176 for a false high when the associated amplification electronics are first turned on and transmitter 104a is not transmitting an ultrasonic pulse to receiver 104b.

In FIG. 8, a table 150 lists equations employed by controller 162 to determine a SamplesPerStroke 152 value. In the example illustrated in this table, the SamplesPerStroke is found to have a value of 21.06 for an R value of 60 (motor shaft RPM). When the shaft of the motor is turning at 60 RPM, the present invention performs 21.06 samples for each pumping cycle of pumping cassette 114.

FIG. 9 shows a table 154 that illustrates the sample volume for a stroke (pumping cycle) of 75 micro liters ($\mu$l) for several different types of tubing having different internal diameters. Also, the sampling percentages for different flow rates through the tubing are displayed.

FIG. 10 illustrates a table 156 that lists variables and their corresponding definitions. These variables are employed by controller 162 for controlling air bubble sensor 176. All volumes are calculated in units of 0.1 micro liters ($\mu$l) and the signal readings of air bubble sensor 176 are in units of the difference (in ADC counts) between post-trigger and pre-trigger readings, unless otherwise specified (the trigger occurs when transmitter 104a produces an ultrasonic pulse for sensing by receiver 104b).

Figure 11:
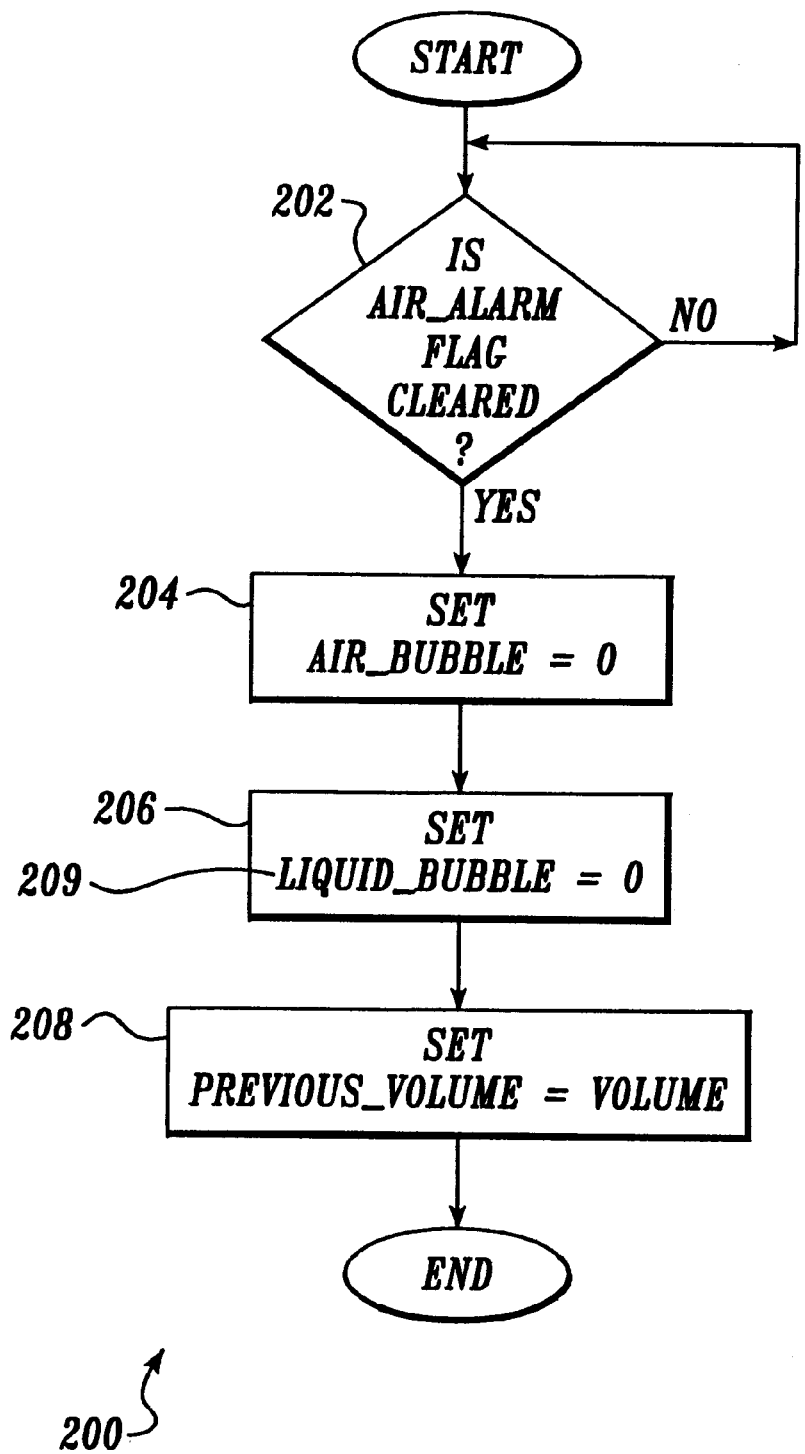
FIG. 11 is a logical block diagram of the steps employed to initialize the variables defined in FIG. 10.

FIG. 11 shows an overview 200 of the steps employed to initialize the values of variables described in FIG. 10, which are employed to control air bubble sensor 176. The logic moves from a start block to a decision block 202 and determines whether the air_alarm flag is clear. If not, the logic loops until the air_alarm flag is cleared. Once this flag is cleared, the logic steps to a block 204 in which an air_bubble variable 207 is set equal to zero. The logic advances to a block 206 in which a liquid_bubble variable 209 is set equal to zero. Moving to a block 208, the logic sets a previous_volume variable 205 equal to the value of a volume variable 203. Thereafter, the logic terminates.

Figure 12:
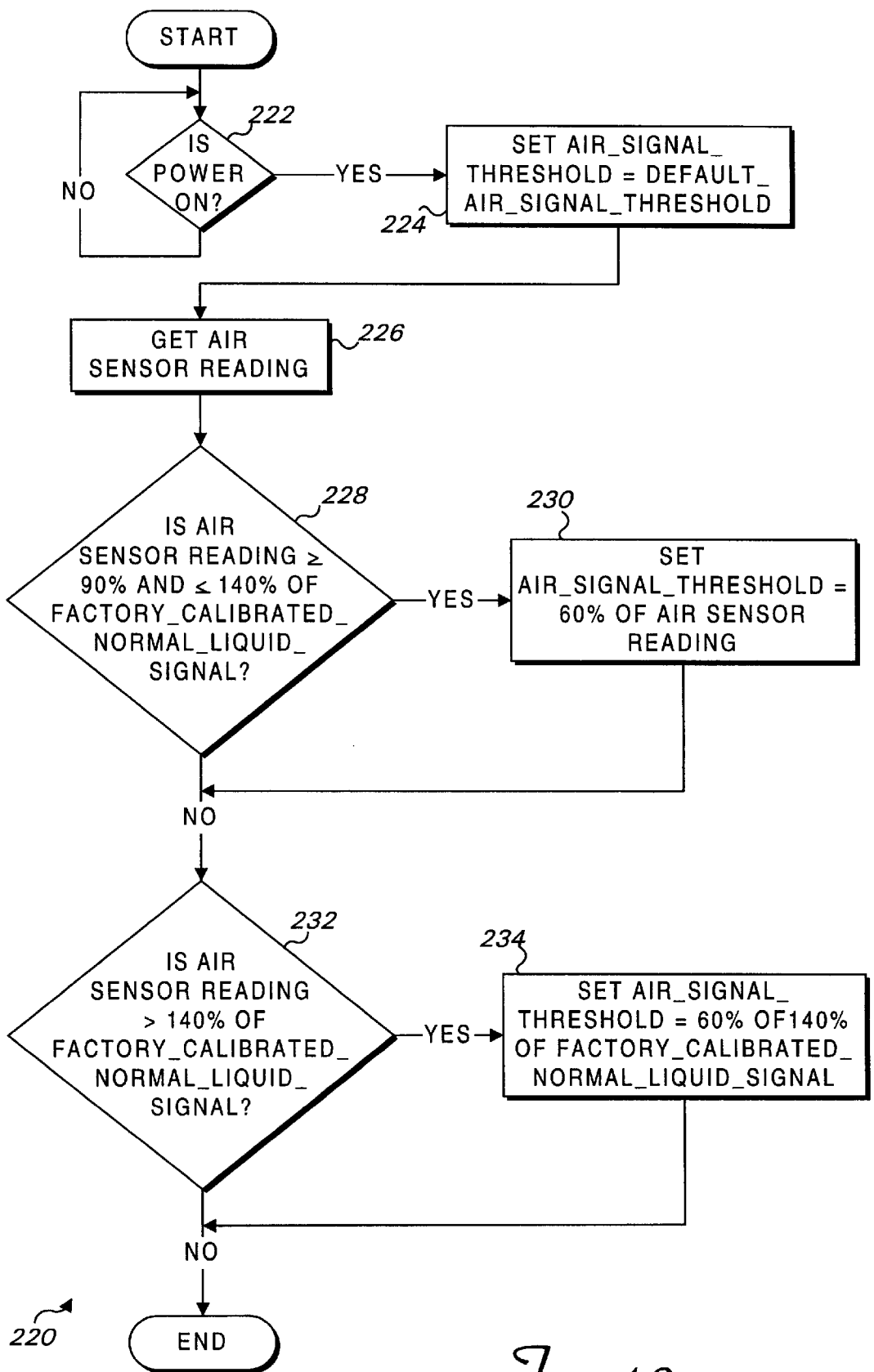
FIG. 12 is a logical block diagram illustrating the steps employed by the control system to reduce false alarms by adjusting the values of several variables defined in FIG. 10.

In FIG. 12, an overview 220 illustrates the steps that are optionally employed at least once every second that pumping cassette 114 is latched into the interior of pump chassis 112. These steps reduce false alarms by "relatively" adjusting the values of several variables described in table 156 of FIG. 10 to compensate for minor contamination of the exterior surface of the portion of distal tubing 118 monitored by air bubble sensor 176. These relative adjustments (if implemented) can finesse minor irregularities in pumping or smaller amounts of contamination for a variety of different types of disposable pumping cassettes. However, predetermined set points that control the absolute/safe operation of the system are not adjusted. Instead, the present invention reduces the number of false alarms without reducing the safety provided by the absolute values.

For example, the system might normally detect values of 70 and 20 (i.e., of the signal produced by receiver 104b), as indicative of the presence in the distal tubing of fluid and air, respectively. However, if the exterior surface of distal tubing 118 becomes slightly contaminated, then these values may rise to 150 for fluid and 80 for air. The present invention compensates for these changes so long as the predetermined absolute values for the presence of fluid and air are not exceeded, e.g., 200 for fluid and 130 for air. While a current embodiment that is soon to be commercially introduced will not includes this feature, in some cases it may be desirable to include these steps in the logic used with monitoring the air bubble sensor.

Moving from a start block to a decision block 222, the logic determines if power has been applied to the IV pump, i.e., to energize the motor. If false, the logic continuously loops until the determination is true. When the determination at decision block 222 is true, the logic steps to a block 224 and an air_signal_threshold variable 213 is set equal to a default_air_signal_threshold value 217.

Moving to a block 226, the logic fetches a signal reading for the signal output from air bubble sensor 176. In a decision block 228, the logic determines if the signal reading is greater than or equal to 90% and less than or equal to 140% of the value of factory_calibrated_normal_liquid_signal 219. If the signal reading is within this range, the logic steps to a block 230 and air_signal_threshold variable 213 is set equal to a value of 60% of the actual signal reading of the air bubble sensor 176. The logic then advances to a decision block 232 from block 230, and also proceeds to decision block 232 if the determination at decision block 228 was false (i.e., the reading is outside the range). At decision block 232, the signal reading of air bubble sensor 176 is compared to a value greater than 140% of the value of factory_calibrated_normal_liquid_signal 219. If the reading is greater than the factory_calibrated_normal_liquid_signal, the logic steps to a block 234, in which air_signal_threshold 213 is set equal to 60% of 140% (i.e., 84%) of factory_calibrated_normal_liquid_signal 219. Lastly, the logic returns to the main flow of the control logic. Also, if the determination at decision block 232 is false the logic returns to the main flow.

Figure 13:
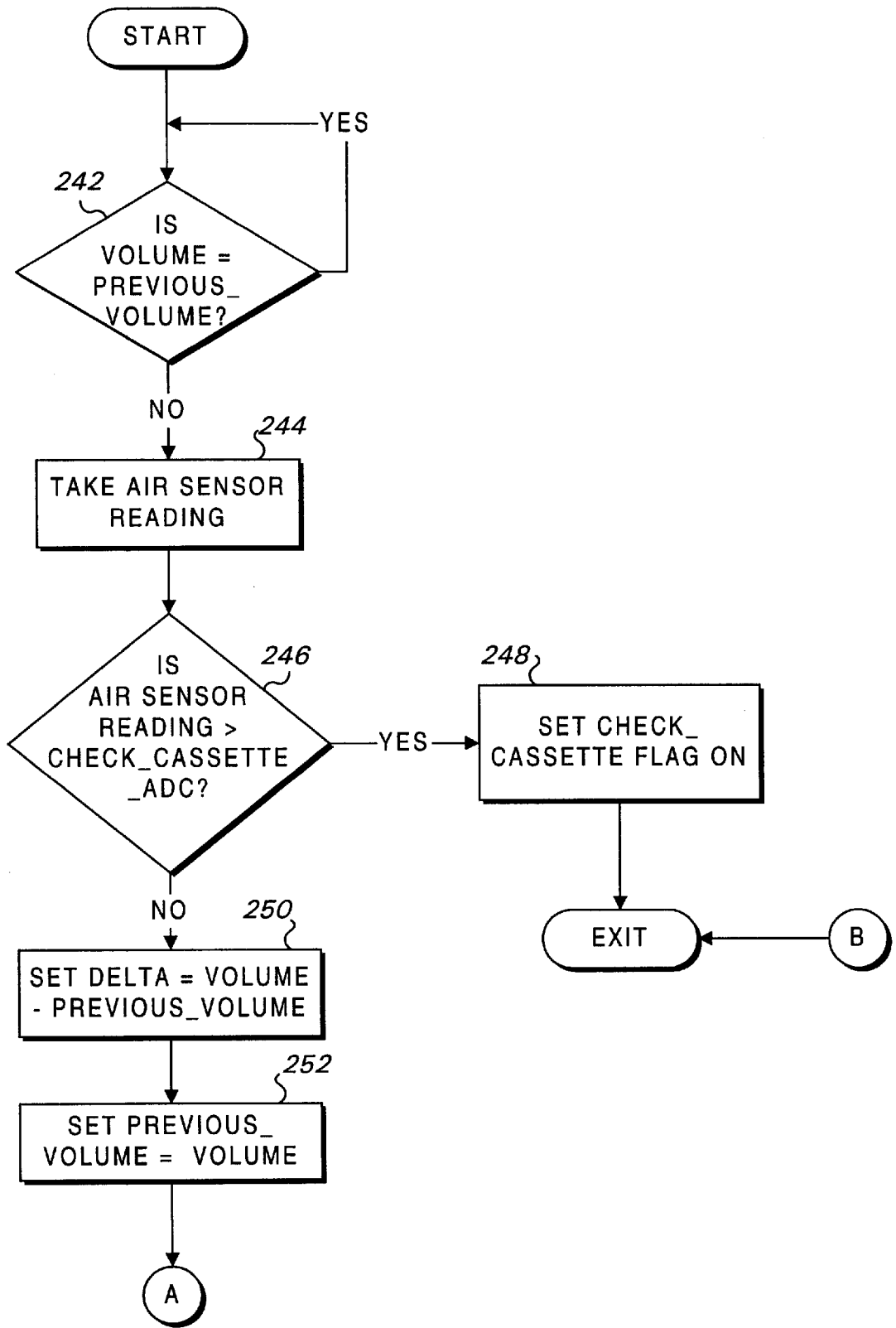
FIG. 13 is a logical block diagram showing the steps performed each time the signal produced by the air bubble sensor is sampled.

In FIG. 13, a general overview 240 is shown of the logical steps performed each time during sampling interval (1.29/R) for air bubble sensor 176, using several of the variables defined in table 156 of FIG. 10. From a start block, the logic advances to a decision block 242 and determines if volume variable 203 is equal to previous_volume variable 205. If not, the logic continuously loops until this determination is negative. Next, the logic steps to a block 244 in which a signal reading (resulting from an analog to digital conversion of the electrical signal produced by receiver 104b) from air bubble sensor 176 is fetched. Advancing to a decision block 246, the logic determines if the signal reading of air bubble sensor 176 is greater than a check_cassette_adc_value 221. If true, the logic moves to a block 248 and a check_cassette flag (alarm) is set on. Then, the logic advances to an exit block and terminates.

Figure 14:
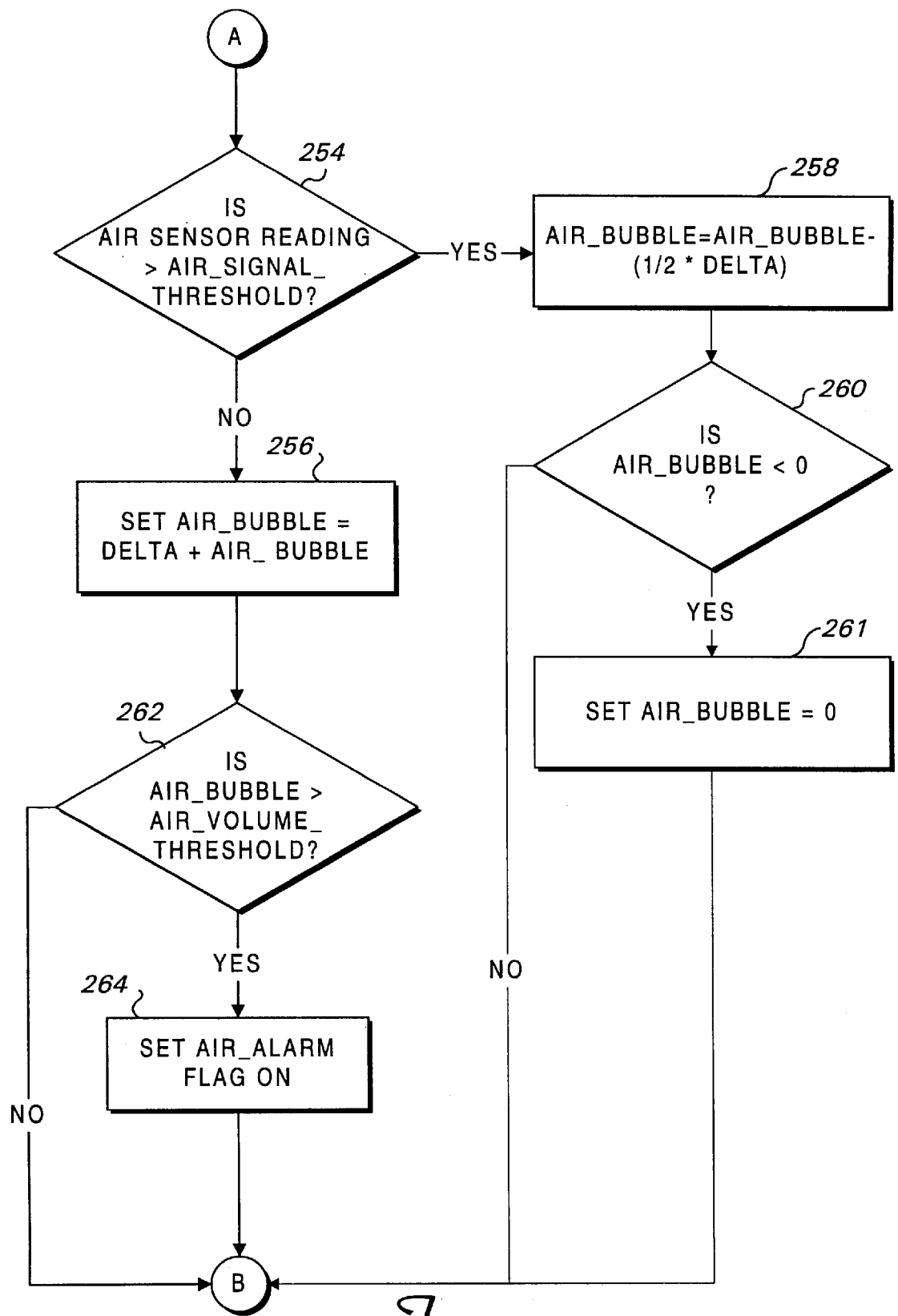
FIG. 14 is a continuation of the logical block diagram illustrated in FIG. 13.

However, if the determination at decision block 246 is false, the logic flows to a block 250 and delta variable 201 is set equal to the value of volume variable 203 minus the value of previous_volume variable 205. At a block 252, the value of previous_volume variable 205 is set equal to the value of volume variable 203. Referring to the continuation of this flow chart in FIG. 14, the logic next moves to a decision block 254 in which it determines if the signal reading of air bubble sensor 176 is greater than air_signal_threshold variable 213. If false, the logic flows to a block 256, and the air_bubble variable 207 is set equal to the value of delta 201 plus the prior value of air_bubble variable 207.

If the determination at decision block 254 is true, the logic steps to a block 258 in which the air_bubble variable is set equal to the difference between its previous value and one-half the delta value. The logic then advances to a decision block 260, in which a determination is made as to whether air_bubble variable 207 is less than zero, and if so, the value of air_bubble is set equal to zero in a block 261. Thus, the value of the air_bubble variable is precluded from being negative. If the value of the air_bubble variable is not less than zero in decision block 260, or following block 261, the logic advances to the exit block (FIG. 13). Following block 256, a decision block 262 determines if the value of the air_bubble variable is greater than the air_volume_threshold value, as indicated by reference number 211 in FIG. 10. If so, a block 264 provides for setting the air_alarm flag on. Otherwise, or following block 264, the logic terminates (in FIG. 13).

Figure 15:
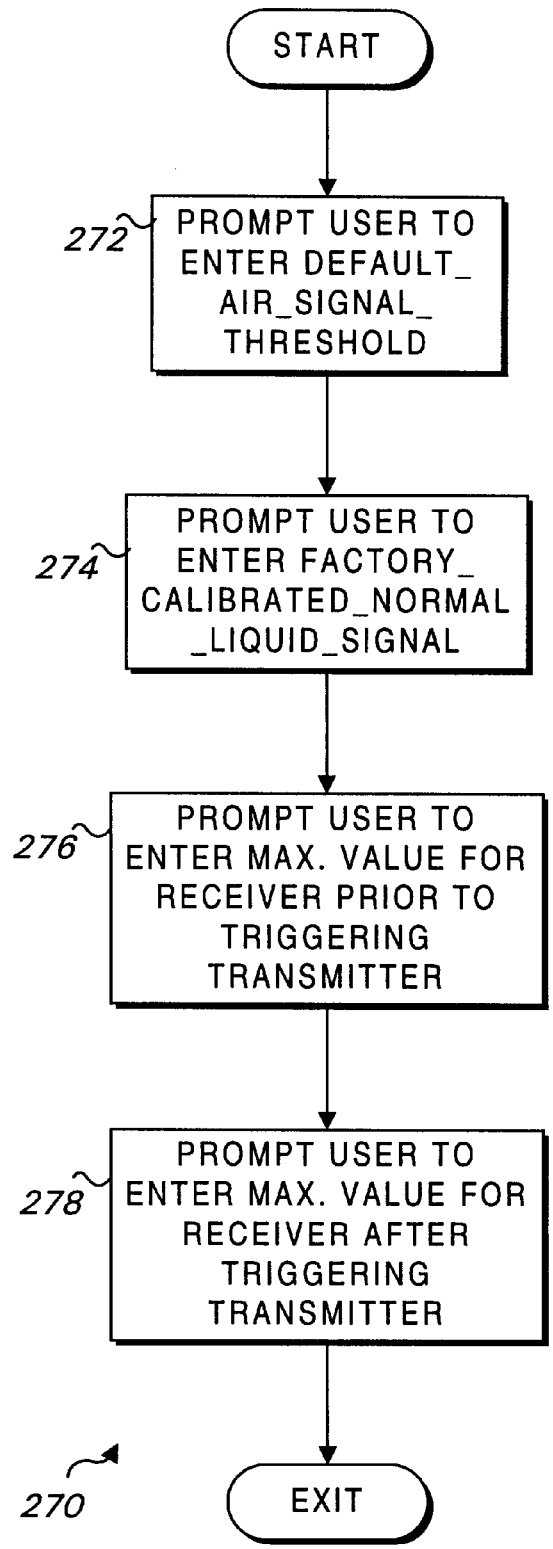
FIG. 15 is a logical block diagram illustrating the steps employed to determine (calibrate) values for several variables defined in FIG. 10.

FIG. 15 illustrates an overview 270 of the steps employed to provide absolute and calibration values for several variables defined in table 156 of FIG. 10. The logic moves from a start block to a block 272 to provide an output on the display that prompts the user to enter a value for a default_air_signal_threshold variable 217. Stepping to a block 274, another prompt is provided to the user to enter a value for factory_calibrated_normal_liquid_signal 219. At a block 276, the user is prompted to enter a maximum signal value produced by air bubble sensor 176, i.e., the signal value generated prior to triggering output of an ultrasonic pulse from transmitter 104a to receiver 104b. In a block 278, the user is prompted to enter a maximum signal value produced by air bubble sensor 176 after the triggering of the ultrasonic pulse. Lastly, the logic moves to the end block and returns to the main flow of logic.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for automatically detecting a gas bubble in a liquid flowing through a tube of an intravenous line having a cassette disposed therein, comprising:
   (a) a chassis;
   (b) a transmitter for generating an acoustic signal that is directed through a portion of the tube, the transmitter being disposed at one side of the tube, in contact therewith;
   (c) a receiver for receiving the acoustic signal and producing an electrical signal in response thereto, the receiver being in contact with an opposite side of the tube, directly opposite the transmitter; and
   (d) a pair of members, each member of the pair being pivotally coupled to and supported by the chassis, one member supporting the transmitter, another member supporting the receiver, the pair of members being pivoted in an outwardly direction in response to engagement between the cassette and the pair of members, said members being pivoted in an inwardly direction to position the transmitter and the receiver in contact with the opposite sides of the tube, a magnitude of the electrical signal produced by the receiver indicating whether a gas bubble is disposed in the tube between the receiver and the transmitter.

2. The system of claim 1, further comprising a controller that comprises:
   (a) a processor, the processor being coupled to the transmitter to sample the electrical signal produced thereby; and
   (b) a memory coupled to the processor, the memory storing machine instructions that define a plurality of functions that are implemented when the machine instructions are executed by the processor, said plurality of functions including:
      (i) initializing a plurality of variables;
      (ii) calibrating the electrical signal at a periodic time interval;
      (iii) sampling the electrical signal at another periodic time interval, producing samples; and
      (iv) employing each sample of the electrical signal to determine at least one of an amount of liquid and a size of the gas bubble in the portion of the tube.

3. The system of claim 2, wherein the function of initializing comprises the functions of setting at least one of:
   (a) a gas volume variable equal to zero, the gas volume variable being subsequently used to accumulate a total volume of gas bubbles detected in the portion of the tube; and
   (b) a liquid variable equal to zero, the liquid variable indicating an amount of the liquid that has flowed through the tube.

4. The system of claim 3, wherein the functions further include determining a minimum value for an amount of the liquid that must flow through the tube before the gas volume variable is reset to zero.

5. The system of claim 2, further comprising an input device, wherein the function of initializing includes the functions of:
   (a) prompting a user to enter a default value for at least one of the variables on the input device; and
   (b) prompting the user to enter a maximum value for the electrical signal on the input device.

6. The system of claim 2, wherein the function of calibrating comprises the functions of:
   (a) employing a threshold value to determine whether a value associated with the electrical signal corresponds to a predetermined range, the threshold value being a minimum for the electrical signal that is indicative of liquid in the portion of the tube; and if so,
   (b) determining another threshold value indicating that the portion of the tube is contaminated, said other threshold value comprising a new minimum for the electrical signal that is indicative of liquid in the portion of the tube.

7. The system of claim 3, wherein the function of employing each sample of the electrical signal to determine at least one of the amount of the liquid and the size of the gas bubble flowing through the tube comprises the functions of:
   (a) determining that a sample indicates the liquid in the portion of the tube; and
   (b) setting the gas bubble variable as a function of a change in the amount of the liquid currently in the portion of the tube.

8. The system of claim 2, further comprising an alarm, wherein the plurality of functions further include:
   (a) determining if the electrical signal corresponds to a predetermined value associated with an alarm; and if so,
   (b) energizing the alarm to alert a user.

9. The system of claim 8, wherein the plurality of functions further include:
   (a) determining whether the magnitude of the electrical signal indicates that liquid has not flowed through the portion of the tube for a predetermined volume of delivery; and if so,
   (b) energizing the alarm to alert the user.

10. The system of claim 8, wherein the plurality of functions further include:
    (a) determining whether the magnitude of the electrical signal indicates that only gas has flowed through the portion of the tube for a predetermined volume of delivery; and if so,
    (b) energizing the alarm to alert the user.

11. The system of claim 8, wherein the plurality of functions further include:
    (a) determining whether the magnitude of the electrical signal indicates that power is not being supplied to a portion of the system; and if not,
    (b) energizing the alarm to alert the user.

12. The system of claim 2, further comprising a display, and an input device, wherein the plurality of functions further include employing the display to prompt the user to input a value for a particular parameter on the input device for calibration purposes.

13. The system of claim 12, wherein the particular parameter includes at least one of an absolute calibration value and an absolute operation value.

14. The system of claim 2, wherein the controller is adapted to connect to a motor of a pump, the controller only sampling the electrical signal when the motor is energized to actuate the pump.

15. The system of claim 14, wherein the transmitter and receiver are only energized to detect a gas bubble when the motor is energized to actuate the pump, and to determine if the pump is flooded when the motor is not moving.

16. The system of claim 1, further comprising a spring for applying a biasing force to the members that tends to keep the transmitter and the receiver in contact with the portion of the tube.

17. The system of claim 16, wherein the spring comprises at least one of a helical spring, a torsion spring, and an elastomeric band.

18. The system of claim 16, wherein a spacing between the pair of members is variable, said biasing force maintaining the pair of members in contact with the sides of the tube to accommodate different types of tubes.

19. A system for automatically detecting a gas bubble in a liquid flowing through a tube of an intravenous line, comprising:
   (a) a chassis, said chassis defining a slot that is substantially wider than a diameter of the tube;
   (b) an ultrasonic transmitter that produces an ultrasonic signal directed through a portion of the tube disposed within the slot, the ultrasonic transmitter being disposed adjacent a side of the portion of the tube;
   (c) an ultrasonic receiver for receiving the ultrasonic signal and producing a corresponding electrical signal, the receiver being disposed on an opposite side of the portion of the tube, directly opposite the ultrasonic transmitter;
   (d) a pair of members pivotally connected to the chassis and disposed adjacent opposite sides of the slot, one member having an end facing toward the slot, said ultrasonic transmitter being disposed on said end, another member also having an end facing toward the slot, said ultrasonic receiver being disposed thereon, the pair of members pivoting to position the ultrasonic transmitter and the ultrasonic receiver against the sides of the portion of the tube and as a result, accommodating tubes of different external diameters and different stiffnesses; and
   (e) a controller that is coupled to the ultrasonic transmitter to excite the ultrasonic transmitter at a resonant frequency, so that the ultrasonic transmitter produces the ultrasonic signal, and to the ultrasonic receiver to receive the electrical signal produced thereby in response to the ultrasonic signal, the controller responding to a magnitude of the electrical signal to determine whether a liquid or a gas is in the portion of the tube disposed between the ultrasonic receiver and the ultrasonic transmitter.

20. A method for detecting a gas bubble in a liquid that flows through a tube of an intravenous line and automatically accommodating tubes of different stiffness, comprising the steps of:
   (a) providing a chassis;
   (b) providing a pair of members, each member of the pair pivotably mounted and supported by said chassis, said members pivotable in an outwardly direction in response to engagement between the cassette and the pair of members;
   (c) mounting a receiver and a transmitter to said members respectively to position said receiver and transmitter on opposing sides of a portion of the tube;
   (d) exciting the transmitter to produce an acoustic signal that is acoustically coupled to the receiver through said portion of the tube, and the receiver producing an electric signal that corresponds to an acoustic signal received from the transmitter, a magnitude of said electrical signal being indicative that one of the gas and the liquid is disposed in the portion of the tube;
   (e) periodically sampling the electrical signal produced by the receiver to monitor flow through the tube, detecting said one of the gas and the liquid in the portion of the tube;
   (f) applying a biasing force to pivot the members in an inwardly direction to cause said transmitter and receiver into contact with the portion of the tube, so that tubes having different stiffness are automatically accommodated with sampling the electrical signal.

21. The method of claim 20, further comprising the steps of:
   (a) determining whether a magnitude of the electrical signal corresponds to a predetermined value associated with an alarm condition, and if true,
   (b) providing an alarm signal to alert a user of the alarm condition.

22. The method of claim 20, further comprising the step of periodically calibrating the electrical signal.

23. The method of claim 20, further comprising the step of exciting the transmitter to produce the acoustic signal only when a liquid should be flowing in the portion of the tube, and when detecting that a flooded condition exists.

24. The method of claim 20, further comprising the steps of:
   (a) initializing a plurality of variables;
   (b) repetitively calibrating the electrical signal at a first periodic time interval;
   (c) repetitively sampling the electrical signal at a second periodic time interval, producing samples; and
   (d) employing each sample of the electrical signal to determine at least one of an amount of liquid and a size of a gas bubble in the portion of the tube.

25. The method of claim 24, furthering comprising the step of setting a gas volume variable equal to a function of a change in a volume of the liquid, when liquid is detected in the portion of tube.

26. The method of claim 25, further comprising the step of resetting the gas volume variable to a non-negative value.

27. The method of claim 24, further comprising the steps of:
   (a) prompting a user to enter a default value for at least one of a plurality of variables used in controlling the detection of gas bubbles; and
   (b) prompting the user to enter a maximum delta value for the electrical signal.

28. The method of claim 22, wherein the step of periodically calibrating comprises the steps of:
   (a) employing a threshold value to determine whether a value associated with the electrical signal corresponds to a predetermined range, the threshold value being a minimum for the electrical signal that is indicative of liquid in the portion of the tube; and if so,
   (b) determining another threshold value indicating that the portion of the tube is contaminated, said other threshold value comprising a new minimum for the electrical signal that is indicative of liquid in the portion of the tube.

29. The method of claim 27, wherein the step of employing the samples of the electrical signal to determine the size of the gas bubble flowing through the tube comprises the steps of:

(a) determining if liquid is currently present in the portion of the tube; and if so, (b) setting the gas bubble variable to a function of a change in a volume of the liquid in the portion of the tube.

30. The method of claim 20, further comprising the steps of:

(a) determining if the electrical signal corresponds to a predetermined value associated with an alarm; and if so, (b) alerting a user.

31. The method of claim 20, further comprising the steps of:

(a) determining whether the magnitude of the electrical signal indicates that less than a predetermined volume of liquid has flowed through the portion of the tube; and if so, (b) alerting the user.

32. The method of claim 20, further comprising the steps of:

(a) determining whether the magnitude of the electrical signal indicates that only gas of more than a predetermined volume has flowed through the portion of the tube; and if so, (b) alerting the user.

33. The method of claim 20, further comprising the step of displaying a prompt to the user to input a parameter for use in detecting the gas bubble.

34. The method of claim 33, wherein the parameter includes at least one of an absolute calibration value and an absolute operation value.

35. The method of claim 20, further comprising the step of automatically compensating for a contamination on an outer surface of the portion of the tube in detecting said one of the gas and the liquid in said portion of the tube.

* * * * *